United States Patent [19]

Jenkins et al.

[11] 4,364,386

[45] Dec. 21, 1982

[54] APPARATUS FOR CONVERTING A PUMP TO A CONTROLLER

[75] Inventors: Jon A. Jenkins, Rancho Santa Fe; Herbert A. Schwan, Encinitas, both of Calif.

[73] Assignee: Imed Corporation, San Diego, Calif.

[21] Appl. No.: 213,863

[22] Filed: Dec. 8, 1980

[51] Int. Cl.³ .............................................. A61M 5/00
[52] U.S. Cl. .................................. 128/214 E; 73/705; 73/715; 417/63
[58] Field of Search ....... 128/214 F, 214 E, DIG. 12, 128/DIG. 13; 222/23; 417/705, 715, 360, 63; 73/705, 715, 716; 200/835, 834

[56] References Cited

U.S. PATENT DOCUMENTS

| | | | |
|---|---|---|---|
| 3,100,997 | 8/1963 | Lorenz | 73/705 |
| 3,922,909 | 12/1975 | Dixon et al. | 73/715 X |
| 4,204,538 | 5/1980 | Cannon | 128/214 F X |
| 4,277,227 | 7/1981 | Jenkins | 128/214 E X |
| 4,289,963 | 9/1981 | Everett | 73/705 X |
| 4,303,376 | 12/1981 | Siekmann | 128/214 F X |

*Primary Examiner*—Stephen C. Pellegrino
*Attorney, Agent, or Firm*—Ellsworth R. Roston; Charles H. Schwartz

[57] ABSTRACT

Apparatus controls the maximum pressure of the fluid which can flow through a pump. The apparatus includes a disposable unit with an inlet for receiving fluid from a source, an outlet for transferring the fluid to a patient and a chamber communicating between the inlet and the outlet. A diaphragm across the chamber is constrained in accordance with the pressure of the fluid in the chamber. The diaphragm transmits the constraint to a stiffener.

The disposable unit is removably attached to the pump casing. A knob is externally disposed on the pump casing and is adjustable to control the maximum force of the fluid in the disposable unit. The knob controls the force exerted on biasing means in a first direction. A force is also exerted against the biasing means in a second direction opposite to the first direction. This force is dependent upon the force on the stiffener.

The biasing means may include a spring. The force on the biasing means in the first direction is provided by a back-up member which is pivotable at one end and is disposed against the spring at an intermediate position and is provided with an adjustable lever arm dependent upon the adjustment of the knob. The force in the opposite direction is transmitted by the stiffener to a diaphragm in the pump casing. This diaphragm in turn transmits the force to a vane which is pivotable at one end and is disposed against the spring at an intermediate position. Sensor means are coupled to the vane to provide an output indication after the vane has overcome the bias provided on the spring in the first direction.

31 Claims, 7 Drawing Figures

APPARATUS FOR CONVERTING A PUMP TO A CONTROLLER

This invention relates to apparatus for controlling the pressure at which fluid is pumped from a source to a receiver such as a patient. More particularly, the invention relates to apparatus for limiting within safe limits the pressure at which fluid, such as intravenous fluid, if transferred from a source to a receiver such as a patient.

As medical technology becomes advanced, it becomes increasingly apparent that the care of patients after surgery or in advanced stages of illnesses is quite sensitive and requires the imposition of different parameters for each individual patient. For example, after surgery, each individual patient requires the introduction of different amounts of fluid at preselected rates in accordance with a number of parameters unique to each patient. These parameters include the sex, age, weight and physical condition of the patient. Furthermore, such parameters as the age and physical condition of the patient affect the maximum fluid pressure to which the patient can be safely subjected.

While the patient is quite ill, the fluid is introduced intravenously to the patient. In one mode, a pump is provided to introduce the intravenous fluid at positive pressures from the source to the patient. The use of a pump offers advantages because the pump provides a pressure which assures that the fluid will be introduced intraveneously to the patient. However, it is often difficult to control the pressures of the fluid in the pump so that the pressures are maintained within safe limits. This is particularly true when fluid is introduced intravenously to infants or to persons of advanced age. When the fluid introduced intravenously to infants and to persons of advanced age becomes excessive, the delicate condition of the veins in such patients may prevent the veins of such patient from withstanding such excessive pressures so that the veins may become ruptured. This may be sometimes quite injurious and may be even fatal.

A considerable effort has been made to include in the pumps apparatus for limiting the pressures of the fluid from the pumps to safe limits. In spite of the considerable effort which has been provided for a number of decades to accomplish this, such efforts have not been successful. As on this date, fluid is often pumped intravenously from a source to a patient without sufficient controls to assure that the fluid introduced to the patient will be within safe limits.

This invention provides apparatus which overcomes the above difficulties. The apparatus of this invention is adapted to be used with any pump for controlling, within safe limits, the pressure of fluid, such as intravenous fluid, introduced from a source to a receiver such as a patient. When the pressure of the fluid from the pump exceeds such safe limits, the apparatus of this invention detects such excessive pressure of the fluid and is instrumental in obtaining a discontinuance of the operation of the pump. The apparatus of this invention can be adjusted to any desired pressure limit so that the pressure limit of the fluid introduced to the patient can be varied in accordance with such parameters as the age, sex and physical condition of the patient. The apparatus of this invention is also advantageous because it can be removably coupled to the pump to maintain the operation of the pump within safe pressure limits.

When the apparatus of this invention is coupled to the pump, a knob on the face of the pump may be adjusted to control the pressure limits established by the apparatus of this invention. However, when the apparatus of this invention is not coupled to the pump, the pump operates in its normal fashion to provide an introduction of the fluid to the receiver such as the patient at pressures which are dependent upon the operation of the pump and which sometimes may vary from the pressures expected from the pump.

The apparatus of this invention includes a disposable unit having an inlet for receiving fluid from a source, an outlet for transferring the fluid to a receiver such as the patient and a chamber communicating between the inlet and the outlet. A diaphragm across the chamber is constrained in accordance with the fluid in the chamber. The diaphragm transmits the constraint to a stiffener.

The disposable unit is removably attached to the pump casing. A knob is externally disposed on the pump casing and is adjustable to control the maximum pressure of the fluid in the disposable unit. The knob controls the force exerted on biasing means in a first direction. A force is also exerted against the biasing means in a second direction opposite to the first direction. This force is exerted by the fluid in the chamber and is dependent upon the force exerted on the stiffener by the fluid in the chamber.

The biasing means may include a spring. The force on the biasing means in the first direction is provided by a backup member which is pivotable at one end and is disposed against the spring at an intermediate position and is provided with an adjustable lever arm dependent upon the adjustment of the knob. The force in the opposite direction is transmitted by the stiffener to a diaphragm in the pump casing. This diaphragm in turn transmits the force to a vane which is pivotable at one end and is disposed against the spring at an intermediate position. Sensor means are coupled to the vane to provide an output indication after the vane has overcome the bias provided on the spring in the first direction. When the sensor means provides an output indication, the operation of the pump may be discontinued because the pressure of the fluid introduced intravenously to the patient exceeds a particular maximum limit.

The apparatus of this invention may be used with a pump disclosed and claimed in U.S. Pat. No. 3,985,133 issued on Oct. 12, 1976, for an "IV Pump" and assigned of record to the assignee of record of this application. One of the features of the pump of U.S. Pat. No. 3,985,133 is that a disposable cassette is removably coupled to the pump and is operative to provide a transfer of fluid from a source to a patient. The pump and the cassette are operably associated so that the fluid flows only through the cassette and not through the pump.

The apparatus of this invention is adapted to be removably coupled to the pump so that the fluid flows through the cassette and through the disposable unit of this invention from the source to the patient without flowing through the pump. In this way, the cassette disclosed in patent 3,985,133 and the disposable unit of this invention can be coupled to the pump for a particular patient and can be easily removed from the pump after the introduction of fluid to the patient. The pump can then be used for another patient without any requirement of sterilizing the pump. This can be accomplished by coupling another unit of the cassette and another unit of the disposable unit of this invention to the pump.

IN THE DRAWINGS

Figure 1:
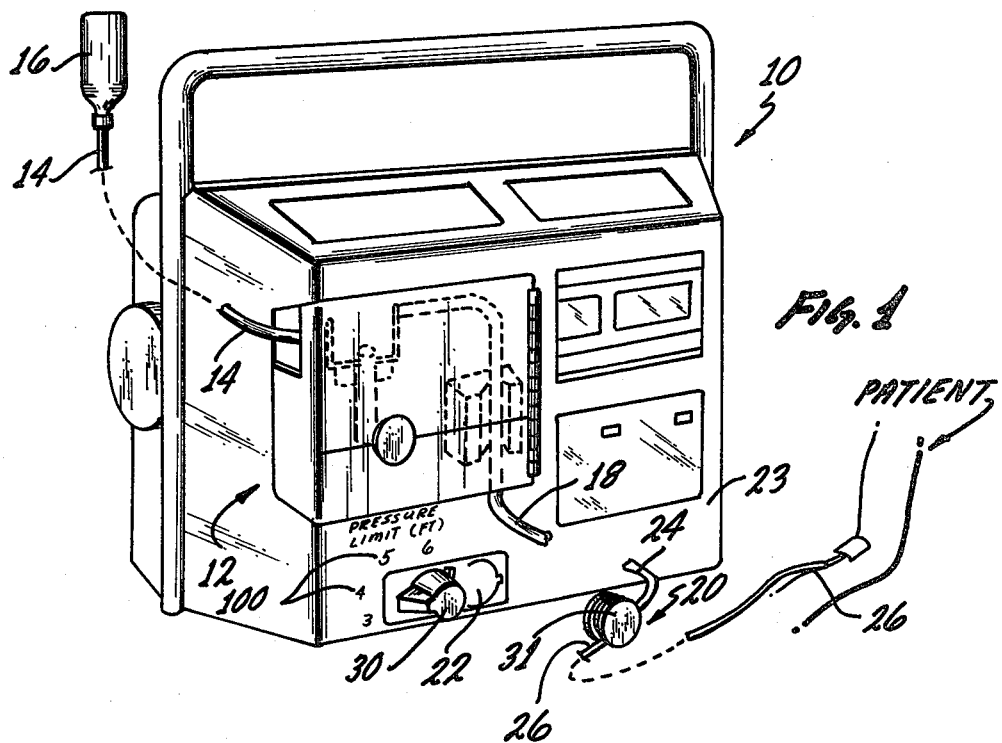
FIG. 1 is a schematic perspective view of a pump, a disposable cassette removably coupled to the pump and a disposable unit removably coupled to the pump for maintaining the flow of fluid from a source to a receiver such as a patient within adjustable limits of pressure.

The apparatus of this invention is adapted to be operated with any pump for maintaining within adjustable limits the pressure of the fluid passing through the pump. However, for the purposes of explanation, the apparatus of this invention is described as being operated with a pump generally indicated at 10 in FIG. 1. This pump may be constructed in a manner similar to that disclosed and claimed in U.S. Pat. No. 3,985,133 assigned of record to the assignee of record of this application.

The pump 10 is adapted to be operated in conjunction with a cassette, generally indicated at 12, removably coupled to the pump. The cassette is provided with an input line 14 extending from a source 16 and with an output line 18 extending to a patient. The cassette 12 is also disclosed and claimed in U.S. Pat. No. 3,985,133.

A disposable unit is included in this invention and is generally indicated at 20. The disposable unit 20 is adapted to be removably disposed in a socket 22 in the front panel 23 of the pump 10. The disposable unit 20 is provided with an input line 24 which actually may constitute an extension of the output line 18 from the cassette. The disposable unit 20 is also provided with an output line 26 which extends to the patient. When the disposable unit 20 is properly inserted into the socket 22, fluid flows from the source 16 through the line 14, the cassette 12, the line 18, the disposable unit 20 and the output line 26 to the patient.

When the pressure of the fluid reaches a particular limit dependent upon the positioning of an adjustable knob 30 on the face of the pump 10, an output indication is provided in the pump. This output indication may be instrumental in discontinuing the operation of the pump to prevent the patient from being injured by excessive pressures of the fluid being introduced to the patient.

The disposable unit of this invention includes a housing 31 made from a suitable material such as a plastic. The housing 31 is in the form of a hollow button defining an inlet 32 for receiving the line 24 and an output 34 for receiving the line 26. A chamber 36 communicates with the lines 24 and 26.

The chamber 36 is closed at one end by a diaphragm 38 made from a resilient material such as rubber. The diaphragm 38 is provided at each end with rounded eyes 40 which are disposed in sockets in the housing 30 to retain the ends of the diaphragm in a fixed relationship with the housing. The diaphragm 38 is provided with a reinforcement 42 at an intermediate position between the eyes 40. The reinforcement 42 is disposed in an opening 44 in the housing.

The opening 44 communicates with a narrowed passage 46 which extends through the housing 31. A stiffener 48 is provided with a flat portion 50 which is disposed in flush relationship with the diaphragm 38 in the opening 44 in the housing. A tubular portion 52 extends through the passage 46 in integral relationship with the flat portion 50.

The housing 31 is provided with a detent portion such as a shoulder portion 56. When the housing 31 is inserted into the socket 22 in the front panel 23 of the pump 10, it engages detent members 62 defined by leaf springs. These detent members 62 are attached to the front panel 23 of the pump 10. Since the detent members 62 constitute leaf springs, the housing 31 can be easily inserted into the socket 22 in coupled relationship with the detent members 62 or the housing 31 can be easily removed from the socket.

When the housing 31 is inserted into the socket 22 in coupled relationship with the detent members 62, the stiffener 48 engages a diaphragm 64 made from a suitable material such as rubber. The diaphragm 64 is retained within the pump by the disposition of rounded eyes 66 in appropriate sockets in the pump. The diaphragm 64 is provided with a reinforcing portion 68 at an intermediate position between the rounded eyes 66.

The reinforcing portion 68 is disposed in coupled relationship with a hollow barrel portion 70 of a vane 72. The hollow barrel portion 70 of the vane 72 extends through an opening 74 in a support member 76 which is attached to the casing 23 and which defines at least a portion of the support for the diaphragm 64. The vane has protrusions 78 which rest on the support member 76 and which define fulcrums for the pivotal movement of the vane relative to the support member. The vane 72 has a projection 80 at the end opposite the protrusions 78.

A backup member 82 is disposed in spaced relationship to the vane 72 by screws 84 which extend through the member 82 to the support member 76. Springs 86 are disposed around the screws 84 to maintain the back-up member 82 in proper relationship to the support member 76. A spring 88 is also disposed between the vane 72 and the back-up member 82 at an intermediate position along the vane and the back-up member to provide a biasing force against the vane.

A cam 90 is shaped to define a tooth 92 which is disposed against the back-up member 82 at one end of the back-up member. The cam 90 is mounted on a shaft 94 for rotation with the shaft. The shaft 94 is in turn mounted on the housing 60 for rotation relative to the housing. The knob 30 is disposed on the shaft 94 and is manually operable to rotate the shaft 94 and the cam 90. The knob 30 is provided with a pointer 98 to provide for a visual indication of the setting of the knob relative to indications 100 on the face of the pump 10. The indications 100 represent different limits of pressure which can be applied to the fluid passing through the chamber 36 from the source 16 to the patient.

A pair of spaced extensions 102 are provided on the back-up member and are disposed in a direction facing the projection 80 in the vane 72. The extensions 102 are spaced to receive the projection 80 between them. A source of energy such as a light source 104 is disposed on one of the extensions 102, and a sensor such as a photocell 106 is disposed on the other extension. The sensor 106 is connected in an electrical circuit 108 to control the operation of the pump 10. For example, during the time that the sensor 106 is energized, the switch 108 is closed to obtain the operation of the pump 10.

When the knob 30 is rotated, it controls the positioning against the back-up member of the tooth 92 on the cam 90. For example, as the cam 90 is rotated in one direction, the tooth 92 is positioned at progressive positions toward the spring 88. This causes the pivotable arm between the spring 88 and the fulcrum represented by the position of contact of the tooth on the back-up member 82 to become shortened. This reduction in the length of the lever arm causes the force applied by the spring 88 against the vane 72 to become reduced.

In like manner, rotation of the knob 30 in the opposite direction causes the positioning of the tooth 92 to become rotated in a direction to displace the tooth away from the spring 88. This causes the distance of the lever arm between the spring 88 and the tooth 92 to become increased so that the force exerted by the spring on the vane 72 becomes increased.

The pressure of the fluid flowing through the line 24, the inlet 32, the chamber 36, the outlet 34 and the line 26 controls the force exerted on the vane 72 in a direction opposite to the direction of the force exerted on the vane by the spring 88. The pressure of such fluid is transmitted as a force to the diaphragm 38, which in turn applies such force against the diaphragm 64 by transmittal through the stiffener 48. The diaphragm 64 in turn applies such force against the vane 72.

As the pressure of the fluid in the chamber 36 progressively increases, the force applied by the diaphragm 64 against the vane 72 increases in a like manner. At a particular pressure of the fluid in the chamber 36, the force applied against the vane 72 by the diaphragm 64 will become greater than the force applied in an opposite direction against the vane 72 by the spring 88. This particular pressure is dependent upon the setting of the knob 30.

Figure 2:
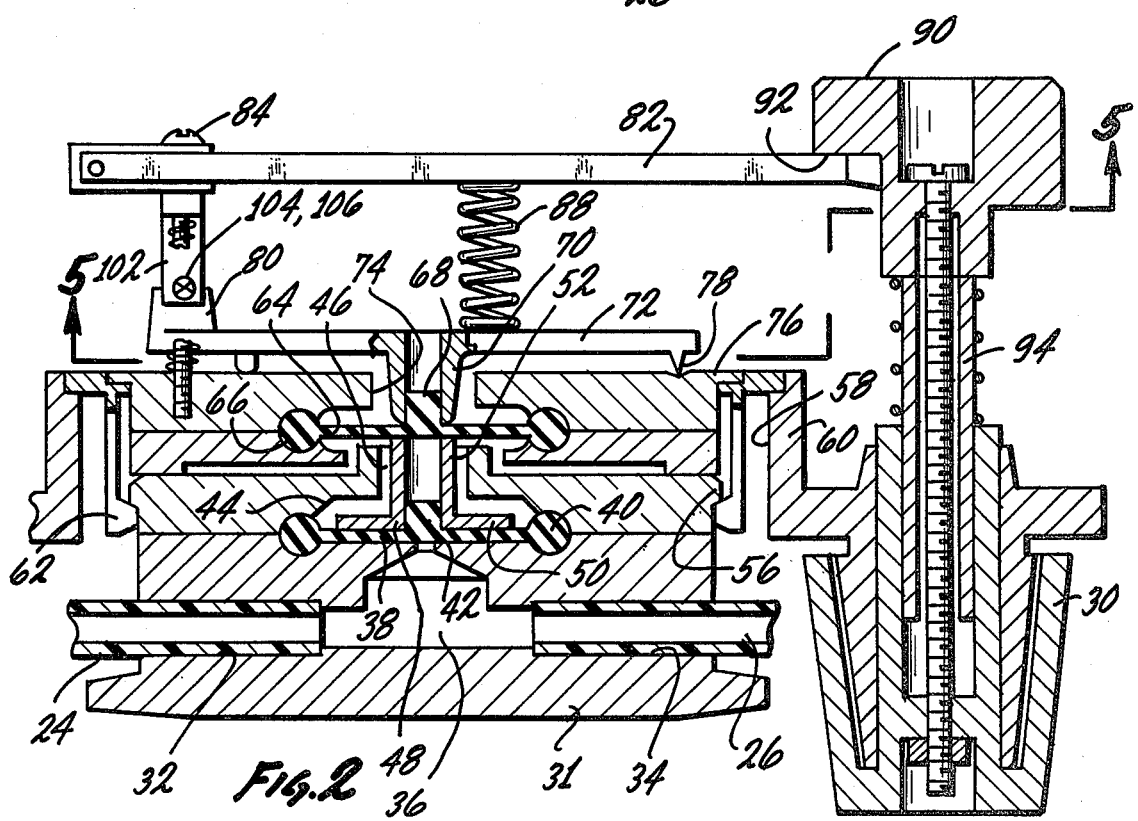
FIG. 2 is an enlarged sectional view of the pump and the disposable unit removably coupled to the pump for maintaining within adjustable limits the pressure of the fluid flowing through the disposable unit from the source to the patient.
Figure 3:
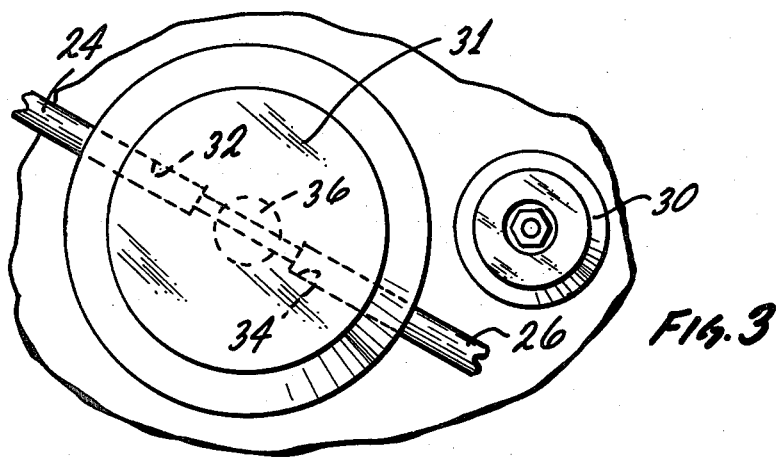
FIG. 3 is an enlarged fragmentary top plan view of the pump and the disposable unit shown in FIG. 2.
Figure 4:
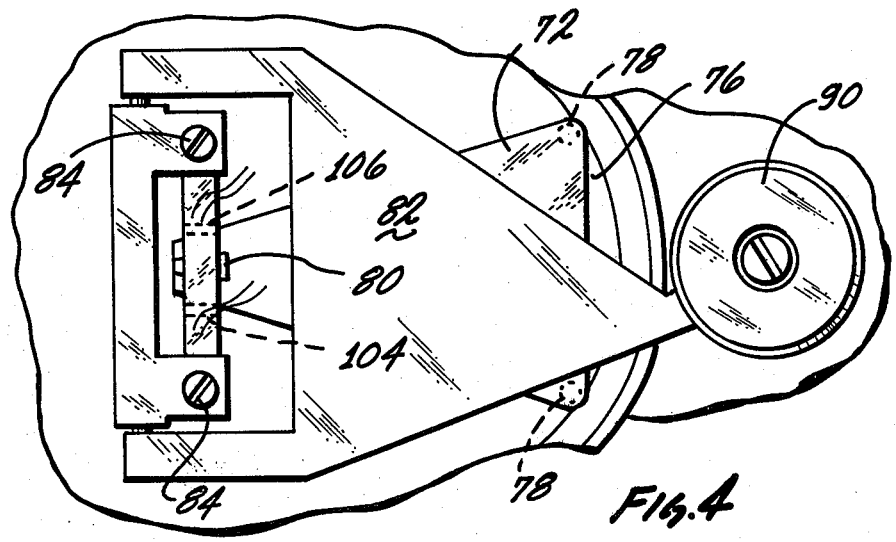
FIG. 4 is an enlarged fragmentary bottom plan view of the pump and the disposable unit shown in FIG. 2.
Figure 5:
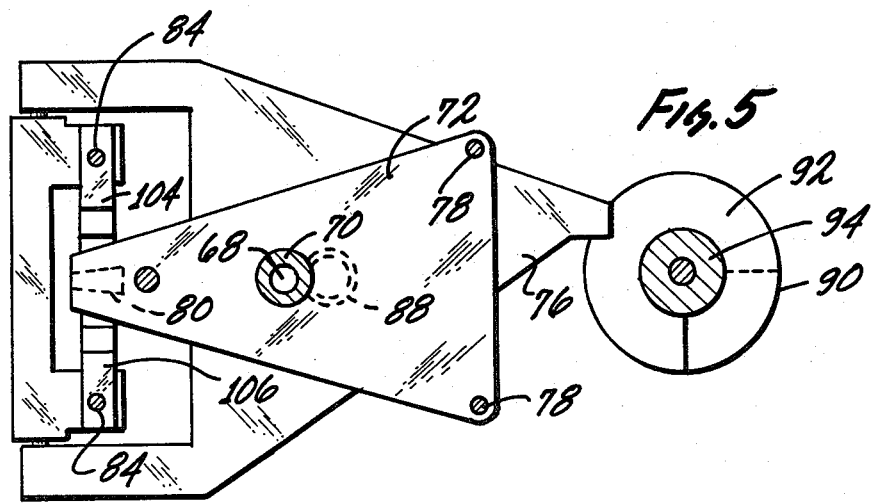
FIG. 5 is a sectional view of the pump and the disposable unit and is taken substantially on the line 5—5 of FIG. 2.
Figure 7:
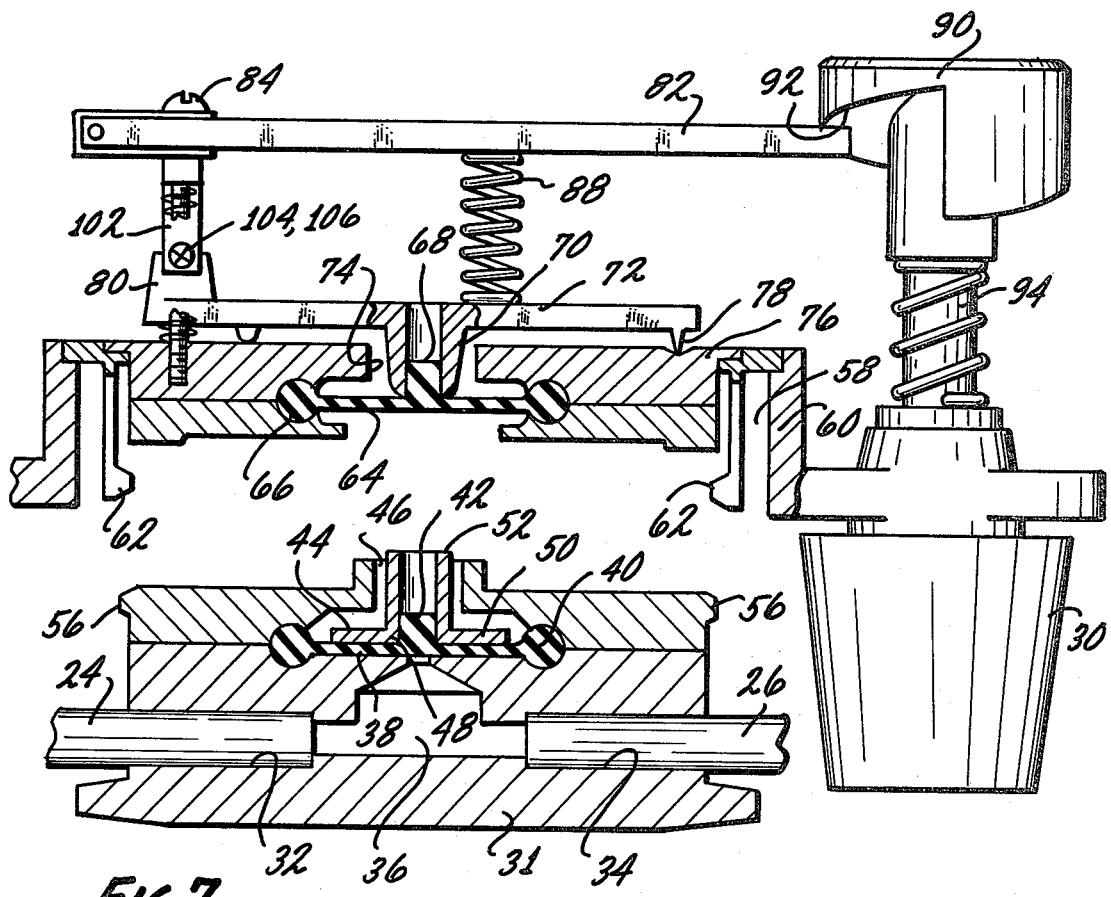
FIG. 7 is a sectional view of the pump and the disposable unit with the disposable unit separated from the pump but positioned to be coupled to the pump.
Figure 6:
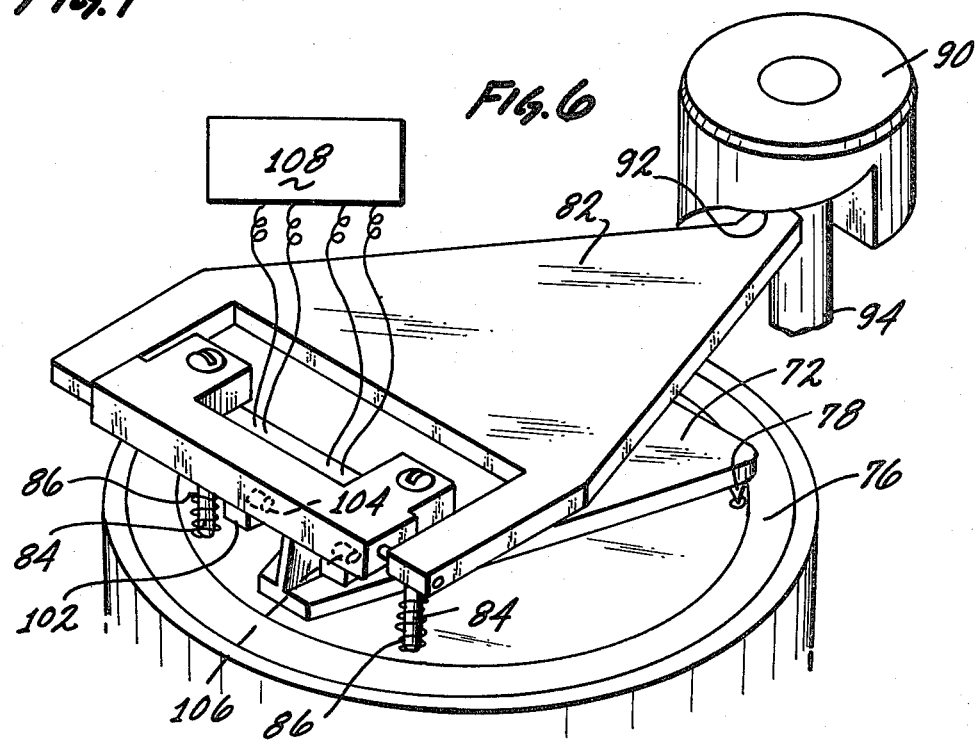
FIG. 6 is a perspective view of the apparatus constituting this invention and illustrates the apparatus from a position above the apparatus.

When the force applied against the vane 72 by the diaphragm 64 exceeds the force applied against the vane by the spring 88, the vane 72 is pivoted upwardly in FIG. 2 about the protruberances 78 as fulcrums. This causes the projection 80 to move into the space between the extensions 102. The pivotal movement of the vane 72 is represented by the broken lines shown in FIG. 2.

Upon a movement of the projection 80 into the space between the projections 102 for a sufficient distance to block the passage of light from the light source 104 to the photocell 106, the signal produced in the photocell is interrupted. This causes the circuit 108 to become opened and the operation of the pump 10 to become discontinued. The passage of fluid from the source 16 to the patient accordingly becomes interrupted when the pressure of the fluid in the chamber 36 exceeds a particular limit dependent upon the adjustable setting of the knob 30.

The apparatus constituting this invention has certain important advantages. It operates in conjunction with a pump such as the pump 10 to control within particular limits the pressure of the fluid introduced by the pump from a source to a receiver such as a patient. The apparatus is particularly advantageous when it is used with a pump for limiting the maximum pressure of the fluid applied by the pump from the source to the patient.

The apparatus of this invention also has other important advantages. This results from the fact that the apparatus is responsive to the difference between two counterbalancing forces, the first dependent upon the adjustable setting of a knob such as the knob 30 and the second dependent upon the pressure of the fluid introduced to the patient. Because of these two counterbalancing forces, an output indication is not produced until the force resulting from the pressure of the fluid exceeds the oppositely imposed force. However, when the force resulting from the pressure of the fluid exceeds the oppositely imposed force, the apparatus of this invention operates in a positive and reliable manner to indicate that the pressure limits in the fluid introduced to the patient have been exceeded.

Until the force imposed upon the vane 72 by the diaphragm 64 exceeds the force imposed upon the vane by the spring 88, there is no significant change in the positioning of any member including the diaphragms 38 and 64. This results from the fact that the vane 64 remains fixed in position until the force imposed upon the vane 72 from the diaphragm 38 exceeds the force imposed upon the vane by the spring 88. Since the diaphragm 38 remains in fixed position until an excessive pressure of the fluid in the chamber is produced, no variables are introduced which will alter the pressure of the fluid in the chamber. In this way, no variables affecting the output indication are provided until the apparatus of this invention is determining whether the pressure of the fluid in the chamber has reached a particular limit.

There are also other important advantages to the apparatus of this invention. For example, the apparatus of this invention includes a disposable unit which passes fluid to the receiver such as the patient without any passage of the fluid through the pump. Since the pump does not receive the fluid, it can be operated for successive patients without any necessity that the pump be sterilized after each such use. Furthermore, the disposable unit is relatively simple in construction and is also relatively inexpensive so that it can be discarded after the operation of the pump with a particular patient has been completed. Even though the disposable unit is discarded after each such use, the cost to the patient is minimized because the pump does not have to be sterilized after each such use.

The apparatus of this invention also offers other advantages of some importance. For example, the disposable unit is easily inserted into a socket in the pump to operate in conjunction with the pump in providing a control over the maximum pressure of the fluid introduced to the patient. The disposable unit is also easily removed from the pump after each such use.

Even when the disposable unit is not disposed in the socket 22 in the pump 10, the pump operates efficiently to introduce fluid from a source to a patient. Upon the insertion of the disposable unit into the socket 22 in the pump 10, the disposable unit becomes coupled on a positive basis to the pump and co-operates with the pump in controlling the pressure of the fluid flowing from the source to the patient.

Although this application has been disclosed and illustrated with reference to particular applications, the principles involved are susceptible of numerous other applications which will be apparent to persons skilled in the art. The invention is, therefore, to be limited only as indicated by the scope of the appended claims.

We claim:

1. In combination for converting a pump into a controller for controlling within particular limits the pressure of fluid introduced from a source to a patient,
   a housing having an inlet and an outlet for the flow of fluid and having a chamber in communication with the inlet and the outlet,
   a resilient diaphragm disposed in the chamber and constrainable in accordance with the pressure of the fluid in the chamber,
   a member having an adjustable fulcrum and pivotable from the adjustable fulcrum, the member being operatively coupled to the diaphragm for variable positioning pivotably in accordance with the constraint of the diaphragm and the position of the fulcrum,
   means adjustably positioned for providing an adjustment in the position of the fulcrum on the member,
   a light source,
   a photocell,
   means for providing for a variation in the amount of the light passing from the light source to the photocell in accordance with the variations in the positioning of the resilient member, and
   means responsive to a particular change in the passage of the light from the source to the photocell for indicating that the pressure of the fluid within the housing has exceeded the particular limits.

2. The combination set forth in claim 1, including,
   detent means on the housing for providing for a removable attachment of the housing to the pump.

3. The combination set forth in claim 2 wherein
   the pump includes detent means and the removable support means include detent means on the housing for cooperating with the detent means on the pump.

4. The combination set forth in claim 3, including,
   the fulcrum of the pivotable member being adjustable to establish the particular limits,
   vane means operably coupled to the member for receiving a force in a first direction from the member in accordance with the adjustment in the fulcrum of the member, and
   means responsive to the force on the resilient diaphragm for imposing a force on the vane means in a second direction opposite to the first direction in accordance with the pressure of the fluid in the chamber.

5. The combination set forth in claim 4, including,
   a spring disposed between the vane means and the member for transmitting to the vane means the force on the member.

6. In combination for converting a pump into a controller for controlling within particular limits the pressure of fluid introduced from a source to a patient,
   a housing,
   detent means on the housing for releasable attachment to the pump,
   an inlet into the housing for receiving the fluid,
   an outlet from the housing for providing for the transfer of the fluid from the housing,
   a chamber within the housing in communication within the inlet and the outlet,
   a diaphragm disposed across the chamber for constraint in accordance with the pressure of the fluid in the chamber, and
   a stiffener disposed in communication with the diaphragm for transferring the constraint of the diaphragm as a force into the pump, the stiffener including a flat portion disposed against the diaphragm in flush relationship with the diaphragm.

7. The combination set forth in claim 6 wherein
   the diaphragm seals the chamber at one end and wherein the stiffener has a tubular portion which is integral with the flat portion and which extends from the flat portion through the housing for communication with the pump.

8. The combination set forth in claim 7 wherein
   the housing is provided with an opening at one end in communication with the chamber and wherein the diaphragm is disposed across the opening to seal the chamber from the opening and wherein the diaphragm is constrainable in a direction to extend into the opening in accordance with increases in the pressure of the fluid in the chamber and wherein the stiffener is extended through the opening to transfer the constraint of the diaphragm into the pump.

9. The combination set forth in claim 8 wherein
   the housing is shaped to define a button at the end opposite the stiffener to facilitate a manual manipulation of the housing into releasable attachment with the pump and wherein the detent means is disposed on the button.

10. The combination set forth in claim 9 wherein
    a passage extends through the housing and communicates with the opening and has a narrower dimension than the opening and the flat portion of the stiffener is disposed in the opening and the tubular portion extends from the flat portion through the passage.

11. In combination for use with a disposable unit to control the pressure of a fluid flowing from a source to a patient, the disposable unit having a resilient member constrainable in accordance with forces imposed upon the resilient member,
    means for pumping the fluid,
    means disposed in the pumping means for releasably holding the disposable unit for obtaining the flow of fluid from the source to the patient through the disposable unit,
    means disposed on the pumping means and adjustable to provide a first force against the resilient member in a first direction corresponding to a maximum pressure in the fluid flowing from the source to the patient,
    means responsive in the pump to the pressure of the fluid in the disposable unit for producing a second force against the resilient member, in a second direction opposite to the first direction, corresponding to such pressure, and
    means responsive to the difference between the first and second forces on the resilient member for indicating when the pressure of the fluid in the disposable unit exceeds such maximum pressure.

12. The combination set forth in claim 11 wherein
    the pump is provided with a casing and
    the adjustable means is disposed externally of the casing for adjustment and
    the casing is provided with detent means for receiving the disposable unit.

13. The combination set forth in claim 12 wherein
    the responsive means include a spring and further include means responsive to the adjustments in the adjustable means for biasing the spring in accordance with such adjustments to provide the first force and further include means responsive to the pressure of the fluid in the disposable unit for working against the spring bias and further includes means for providing an output indication when the bias of the spring has been overcome.

14. In combination for use with a disposable unit to control the pressure of a fluid flowing from a source to a patient, the disposable unit including a resilient member constrainable in accordance with forces imposed upon the resilient member, a casing, means in the casing for receiving the disposable unit to obtain a flow of fluid from the source to the patient, an adjustable knob supported by the casing to control the maximum pressure of the fluid in the disposable unit in accordance with such adjustment, means disposed within the casing and biasing against the resilient member in a first direction by the adjustable positioning of the knob, means disposed within the casing and responsive to the fluid flowing from the source to the patient for producing, against the resilient member in a second direction opposite to the first direction, a force dependent upon the pressure of the fluid in the disposable unit, and means disposed in the casing and operative to provide an output indication after the bias of the biasing means against the resilient member in the first direction has been overcome by the force on the resilient member in the second direction.

15. The combination set forth in claim 14 wherein the means producing a force in the second direction including a resilient diaphragm constrained in accordance with the pressure of the fluid in the disposable unit and wherein means are operatively associated with the resilient resilient means for translating the constraint on the diaphragm into a corresponding force on the diaphragm and wherein means are associated with the biasing means to provide the output indication.

16. The combination set forth in claim 15 wherein the output indicating means includes a vane and a sensor and the diaphragm acts against the vane in accordance with the constraint of the diaphragm and the vane is pivotable at one end and is disposed against the biasing means at an intermediate position and is pivotable in accordance with the constraint of the diaphragm and the biasing of the biasing means and wherein the indicating means are activated in accordance with a particular pivotable disposition of the vane.

17. The combination set forth in claim 16 wherein the biasing means includes a pivotable back-up member pivotable at one end and defining a lever arm variable in length from the pivotable position in accordance with the adjustments of the knob and further includes a spring constrained at opposite ends by the back-up member and by the vane.

18. In combination in a disposable unit for operating in conjunction with a pump to control within particular limits the pressure of fluid introduced from a source to a patient, a housing having a chamber, detent means on the housing, an inlet for receiving the fluid from the source, an outlet for passing the fluid to the patient, a resilient diaphragm disposed across the chamber to close the chamber and to become constrained in accordance with the pressure of the fluid in the chamber, a reinforcement on the diaphragm at an intermediate position on the diaphragm, an opening disposed in the housing in communication with the reinforcement at the end of the housing opposite the chamber, force-transmitting means disposed in a co-operative relationship with the reinforcement and extending through the opening to produce a force in the pump in accordance with the constraint of the diaphragm, the force-transmitting means constituting a stiffener disposed in co-operative relationship with the reinforcement, there being a passage in the housing in communication with the opening and the passage being provided with narrower dimensions than the opening, and the stiffener having a tubular portion extending through the passage to transmit the force on the diaphragm and having a flat portion integral with the tubular portion and disposed in flush relationship with the resilient diaphragm.

19. The combination set forth in claim 18 wherein the stiffener is hollow and the reinforcement is disposed within the hollow interior of the stiffener.

20. In combination for controlling the pressure of fluid passing from a source to a patient, a pump for pumping fluid from the source to the patient, a casing for the pump, there being a socket in the casing, detent means in the socket, a disposable unit including a housing dimensioned to fit into the socket and including detent means disposed on the housing to co-operate with the detent means in the socket for removably retaining the disposable unit in the socket, there being a chamber in the housing, an inlet disposed in the housing and communicating with the chamber to provide for the introduction of fluid from the source into the chamber, an outlet disposed in the housing and communicating with the chamber to provide for the passage of fluid from the chamber to the patient, a resilient diaphragm disposed in the chamber to close the chamber and constrainable in accordance with the pressure of the fluid in the chamber, means disposed in the pump for producing a force on the diaphragm in a direction opposite to the constraint produced on the diaphragm in accordance with the pressure of the fluid in the chamber, and means disposed in the pump and responsive to the resultant constraint of the diaphragm from the forces in the opposite directions for providing an output indication when the pressure of the fluid in the chamber produces a force on the diaphragm greater than the force produced to oppose the force produced by the fluid in the chamber.

21. The combination set forth in claim 20, including, a knob on the face of the pump casing, the knob being adjustable to different positions for controlling the force on the diaphragm in the opposite direction, and the indicating means including means responsive to the adjustments in the positioning of the knob for providing the output indication when the pressure of the fluid in the chamber has reached the particular limit represented by the adjustments in the positioning of the knob.

22. The combination set forth in claim 21, including, means disposed in the pump and adjustably positioned in accordance with the forces imposed upon such means, means disposed in the pump and responsive to the adjustable positioning of the knob for imposing a first force on the adjustably positioned means in accordance with such adjustable positioning of the knob, means disposed in the pump and responsive to the constraint of the diaphragm from the fluid in the chamber for imposing upon the adjustably positioned means a second force in accordance with such constraint, and means associated with the adjustably positioned means for providing the output indication when the adjustably positioned means becomes positioned by an imbalance of forces resulting from the second force being greater than the first force.

23. The combination set forth in claim 22 wherein the adjustably positioned means are pivotable about a fulcrum and means are provided in the pump for producing the second force on the adjustably positioned means, at a position displaced from the fulcrum, in accordance with the constraint of the diaphragm and wherein means are provided in the pump for producing the first force on the adjustably positioned means in accordance with the adjustable positioning of the knob.

24. The combination set forth in claim 23 wherein the means for producing the first force are pivotable about a fulcrum variable in position in accordance with the adjustable positioning of the knob and the means for producing the first force include a spring displaced from the variable fulcrum and disposed against the adjustably positioned means to produce the first force against the adjustably positioned means with a magnitude dependent upon the length of the lever arm between the variable fulcrum and the spring.

25. In combination for controlling within particular limits the pressure of fluid introduced from a source to a patient, a pump for pumping the fluid from the source at a positive pressure, a housing having an inlet and an outlet for the flow of fluid and having a chamber in communication with the inlet and the outlet, a resilient diaphragm disposed in the chamber and constrainable in accordance with the pressure of the fluid in the chamber, means for removably supporting the housing on the pump, means disposed on the pump for adjustably setting the particular limits for the pressure of the fluid flowing through the chamber, means responsive to the constraint of the diaphragm and the adjustable setting of the particular limits for providing an output indication when the pressure of the fluid in the chamber has reached such particular limits, the indicating means including a member coupled to the diaphragm, and means responsive to the adjustable setting of the particular limits for imposing a force on the member in a direction opposite to the force imposed upon the member by the constraint of the diaphragm the force having a magnitude dependent upon such adjustable setting.

26. The combination set forth in claim 25 wherein the member is coupled to the diaphragm to receive a force in accordance with the constraint of the diaphragm and the adjustment in the setting of the particular limits of pressure.

27. The combination set forth in claim 25 wherein the force-imposing means includes a lever arm variable in length in accordance with the adjustable setting of the particular limits of pressure and further includes means disposed to produce a force against the member in accordance with the variations in the length of the lever arm.

28. In combination for converting a pump into a controller for controlling within particular limits the pressure of fluid introduced from a source to a patient, a pump for directing fluid from the source under pressure, the pump including a casing having a receptacle, a housing removably disposed within the casing for receiving the fluid directed from the source by the pump and for directing the fluid to the patient, resilient means included within the housing for constraint in accordance with the pressure of the fluid in the housing, a knob extending from the pump casing and adjustable in position to control within particular limits the pressure of the fluid within the housing, means responsive to the setting of the knob for imposing on the resilient means a constraint in a direction opposite to the constraint imposed upon the diaphragm by the fluid passing through the housing, and means operatively coupled to the resilient means and the knob for providing an output indication when the resilient means have received from the fluid in the housing a particular constraint exceeding the constraint imposed in the opposite direction in accordance with the setting of the knob.

29. The combination set forth in claim 28, including, resilient detent means in the casing for removably holding the housing, and detent means on the housing for cooperation with the resilient detent means in the casing to provide a removable retention of the housing by the casing.

30. The combination set forth in claim 29, there being a socket in the casing for receiving the housing, the resilient detent means being disposed in the socket.

31. The combination set forth in claim 30, including, means operatively coupled to the knob for producing a force variable in accordance with the adjustments of the knob, means operatively coupled to the resilient means for producing a first force in accordance with the constraint of the resilient means and operatively coupled to the variable force means for producing a counterbalancing force in accordance with the variable force provided by the variable force means, and the output indication means becoming operative to provide an output indication when the first force exceeds the counterbalancing force.

* * * * *